United States Patent
Van Belzen et al.

(10) Patent No.: US 7,816,561 B2
(45) Date of Patent: Oct. 19, 2010

(54) METHOD OF IMPROVING THE CRUSHING STRENGTH AND REDUCING THE DUST FORMATION AND THE CAKING TENDENCY OF UREA, AND UREA COMPOSITION

(75) Inventors: Ruud Van Belzen, Middelburg (NL); Luc Vanmarcke, Lembeke (BE)

(73) Assignee: Yara International ASA, Oslo (NO)

( * ) Notice: Subject to any disclaimer, the term of this patent is extended or adjusted under 35 U.S.C. 154(b) by 586 days.

(21) Appl. No.: 11/631,372

(22) PCT Filed: Jun. 2, 2005

(86) PCT No.: PCT/NO2005/000180

§ 371 (c)(1),
(2), (4) Date: Mar. 16, 2007

(87) PCT Pub. No.: WO2006/004412

PCT Pub. Date: Jan. 12, 2006

(65) Prior Publication Data

US 2008/0041131 A1    Feb. 21, 2008

(30) Foreign Application Priority Data

Jun. 30, 2004    (NO) ................................. 20042770

(51) Int. Cl.
*C05C 9/00*    (2006.01)
*C07C 273/14*    (2006.01)

(52) U.S. Cl. ................................... 564/3; 71/28; 71/30

(58) Field of Classification Search ................ 71/11, 71/64.01, 64.02, 28, 30; 564/3
See application file for complete search history.

(56) References Cited

U.S. PATENT DOCUMENTS 3,195,999 A * 7/1965 Chance ........................ 71/28
3,353,949 A   11/1967 Nau
3,740,346 A    6/1973 Sarrade-Loucheur
4,063,919 A   12/1977 Grano, Jr.
4,283,423 A    8/1981 Watkins et al.
4,587,358 A    5/1986 Blouin
5,032,164 A    7/1991 Sanford et al.

FOREIGN PATENT DOCUMENTS

| CA | 2100017 | 1/1995 |
| WO | 00/66515 | 11/2000 |
| WO | 02/20471 | 3/2002 |
| WO | 2005/040069 | 5/2005 |
| WO | 2005/040072 | 5/2005 |

OTHER PUBLICATIONS

European communication dated Jul. 21, 2009 issued in connection with European Patent Application No. 05 744 876.3 corresponding to the present U.S. application.

G.P. Moss et al., "Nomenclature of Carbohydrates", International Union of Pure and Applied Chemistry and International Union of Biochemistry and Molecular Biology, [Online] 1996, Retrieved from the Internet: URL:http://www.chem.qmul.ac.uk/lupac/2carb /22 [retrieved on Jul. 8, 2009].

* cited by examiner

*Primary Examiner*—Wayne Langel
*Assistant Examiner*—Syed Iqbal
(74) *Attorney, Agent, or Firm*—Wenderoth, Lind & Ponack, L.L.P.

(57) ABSTRACT

The invention relates to a method of improving the crushing strength and reducing the dust formation and the caking tendency of urea particles by the addition of an organic compound to the molten urea, where at least one carbohydrate and optionally a polyvinyl compound is added to the urea. The invention also relates to a composition to be used as a urea additive.

11 Claims, No Drawings

METHOD OF IMPROVING THE CRUSHING STRENGTH AND REDUCING THE DUST FORMATION AND THE CAKING TENDENCY OF UREA, AND UREA COMPOSITION

Method of improving the crushing strength and reducing the dust formation and the caking tendency of urea, and urea composition.

The invention relates to a method of improving the crushing strength and reducing the dust formation and the caking tendency of urea particles by the addition of an organic compound to the urea.

It is generally known that urea particles are subject to crushing during production, storage and transport. Up to 25 wt % of the urea particles may be crushed if the urea fertilizer is moved into a storage bin or storage ship at a relatively high temperature of e.g. more than 40° C. Even though the urea particles as such hardly absorb any moisture and are virtually non-susceptible to caking, high percentages of crushed particles do lead to dust problems with a strong caking tendency.

It is also known that a number of chemical compositions can be used as additives to improve the crushing strength, the caking tendency and the resistance to moisture. Formaldehyde, hexamethylenetetramine and formaldehyde/urea condensate products are applied as crushing strength improvers, while the combination poly(vinyl acetate)/surfactant (U.S. Pat. No. 4,812,158) is used to reduce the caking tendency.

International application WO 00/66515 describes a conditioned fertilizer product comprising urea containing fertilizer and a conditioning amount of lactic acid derived conditioning agent. The conditioning agent is preferably included at a concentration of between about 0.1% by weight and about 5% by weight. The conditioning agent is preferably lactic acid, lactide and/or polylactide. A method for conditioning fertilizer is provided including a step of mixing urea-containing fertilizer and conditioning agent at a temperature of between about 135° C. and about 145° C.

All these additives must either be added in relatively large quantities, or the toxic characteristics make them difficult to handle. Moreover, the use of a surface active component as in poly(vinyl acetate)/surfactant, results in increased foaming when the urea is used for industrial applications, such as resin production, whilst formaldehyde derivatives are unsuitable in the case of melamine production. There is also a major difference with respect to the use of additives. Both formaldehyde derivatives and the compositions according to the invention are admixed to a urea melt. The combination poly(vinyl acetate)/surfactant is, however, sprayed onto a preformed particle.

GB-A-1217106 describes a method of reducing the caking of urea by using a poly(vinyl alcohol) having a high molecular weight as an anticaking additive. More in particular, according to this method, an aqueous solution of the additive is admixed to an aqueous solution of urea. Preferentially, an amount of additive of from 0.005 to 5 wt %, based on the weight of the urea, is admixed. The concentration of the aqueous urea solution is initially 80%, according to the example given; after admixture of the solution of the additive, concentration up to 95% takes place at elevated temperature, after which the urea is allowed to crystallize by cooling.

International application WO 02/20471 discloses a method in which a combination of a polyvinyl compound and inorganic salts is admixed with a urea melt. Both the crushing strength and the impact resistance of the resulting granulate appeared to be improved compared to untreated urea. In addition, the compressibility of the urea was found to be decreased substantially. The latter observation can be a great advantage as the urea granulates will be less prone to deformation upon storage. However, the introduction of inorganic salts, such as aluminium sulphate, in urea results in a strong decrease of the pH upon dissolving the urea in water. This can be a serious disadvantage when using urea for technical applications, such as the production of resins.

International application PCT/EP03/11070 relates to a method for improving the crushing strength, impact resistance and the compressibility of urea granules by the addition of a compound to the molten urea, where said compound comprises both a polyvinyl compound and an organic molecule consisting of 1-10 carbon atoms and 1-10 polar organic groups. The polyvinyl compound is preferably combined with pentaerythritol. In some aspects, it would be of interest to find other urea additives as alternatives to already known additives, particularly additives that would reduce the caking tendency of urea particles.

It was therefore an object of the invention to provide a method by means of which urea having an improved crushing strength as well as a reduced dust formation and a low caking tendency is obtained and by means of which the abovementioned drawbacks are overcome.

It was also an object to find alternative additives to already existing urea additives.

It was a further object that the additives should have a low toxicity.

It has been found that the addition of a composition comprising an organic molecule of the carbohydrate type such as monosaccharide, disaccharide, oligosaccharide, polysaccharide or a mixture thereof, to the urea melt leads to an improvement of both the hardness and the caking tendency of the urea particles formed.

In another embodiment, a composition comprising both a carbohydrate and a polyvinyl compound gives a similar improvement. The organic components can be added either separately to the molten urea or together with the aqueous solution of the polyvinyl compound. According to a preferred embodiment, the total added amount of carbohydrates is at most 5% by weight based on the total amount of urea. The present application relates to an intimate mixture of urea, at least one carbohydrate and optionally a polyvinyl compound, resulting in increased hardness of the composition compared to untreated urea. Preferably the polyvinyl compound is a poly(vinyl alcohol), whereas the carbohydrate can be a mono-, di-, oligo or a polysaccharide or a mixture thereof. Preferred carbohydrates are dextrose, fructose, sucrose, maize starch, potato starch, lactose, maltose, guar and xanthan gum.

The present invention will in its widest scope comprise a method of improving the crushing strength and reducing the dust formation and caking tendency of urea particles by the addition of an organic compound to the molten urea, where at least one carbohydrate and optionally a polyvinyl compound is added to the urea. The added carbohydrate is monosaccharide, disaccharide, oligosaccharide, polysaccharide or a mixture thereof. At most 5 wt % carbohydrate, based on the amount of urea, is added. Preferably, 0.02-2 wt % carbohydrate, based on the amount of urea, is added. A polyvinyl compound of the general formula $(CHX-CHY)_n$, where n=4-10 000, and X and Y independently of one another are selected from the group consisting of a hydrogen atom and a polar organic group, is added. The polar organic group is preferably selected from a carboxylic acid group, an ester group, a hydroxyl group, an amine group or an amide group. X is preferably a hydrogen atom and Y preferably substantially consists of a hydroxyl group. At least 70%, preferably at least 80%, of Y consists of a hydroxyl group. An aqueous solution of the polyvinyl compound having a concentration of from 0.01 to 1 wt %, based on the amount of urea, is added. Preferably, an aqueous solution of the polyvinyl compound having a concentration of from 0.05 to 0.5 wt %, based on the amount of urea, is used. The carbohydrate might be added to the urea as a solid, or dissolved in a solvent or an aqueous solution of the polyvinyl compound or a urea solution before being added to the urea.

The invention also relates to a composition to be used in the method as described above, as a urea additive.

The invention is further described and explained in the following experiments.

To demonstrate the effect of the invention, a number of experiments were carried out, employing methods that are representative for production and for testing the quality of the urea particles produced.

Urea particles were produced by admixing the additive, being in the form of a solid, a viscous liquid or an aqueous solution (having the concentrations indicated in the experiments), with a urea melt consisting of more than 96 w/w % urea and less than 4 w/w % water. Thereafter the urea melt was particulated in a granulation process. The particles were collected and kept in an airtight bottle until the analyses were performed.

The crushing strength was determined by subjecting individual particles of urea of 3.15 mm to a measured force, applied by means of a metal plunger. The force, at which the particle fractures, was taken as a measure of strength. The average strength of 20 particles were reported.

The caking index was measured by the following procedure: An amount of particles was pressurized at 143 kgf (2 bar applied on a surface of 69.96 cm$^2$) for 24 hrs at 27° C. The lump of material was then taken out and broken, the amount of force (kgf) needed for this is taken as a measure for the caking tendency.

Dust formation in the products was measured by the following procedure: Clean air was blown through a glass spouted bed (85 mm in diameter) filled with 400 g of urea particles for 2 minutes at a flow rate of 25 Nm$^3$/h. The dust formation is the weight loss of the product after the air treatment in the spouted bed.

Based on experience, the crushing strength should be >3 kgf, the caking tendency should be <75, and the dust formation should be <~500 mg/kg.

Experiment 1

Different carbohydrates were added to the urea melt, and particulated as described above. The addition of carbohydrates was compared with urea without additive and with a standard product with urea-formaldehyde conditioning agent, UF80 (from Dynea, a mixture of urea/formaldehyde/water in a ratio of 23/57/20).

Table 1 shows the crushing strength, dust formation and caking index for urea, without additive, with urea-formaldehyde conditioning agent and with different carbohydrates.

TABLE 1

| Additive | Crushing Strength (kgf) | Dust formation (mg/kg) | Caking index |
| --- | --- | --- | --- |
| no additive | 1.5 | 800 | 205 |
| 1 wt % UF80 | 3.6 | 400 | 30 |
| 0.4 wt % dextrose | 3.3 | 150 | 63 |
| 0.4 wt % fructose | 3.7 | 325 | 53 |
| 0.8 wt % sucrose | 3.9 | 600 | 75 |
| 0.6 wt % starch (maize) | 3.6 | 650 | 91 |

TABLE 1-continued

| Additive | Crushing Strength (kgf) | Dust formation (mg/kg) | Caking index |
| --- | --- | --- | --- |
| 0.4 wt % starch (potato) | 2.4 | 400 | 120 |
| 0.6 wt % starch (potato) | 2.0 | 375 | 135 |

This experiment shows that both the hardness and caking tendency improved upon addition of the carbohydrates. The quality can be as good as or even better than a product treated with formaldehyde, especially with respect to the dust formation.

Experiment 2

An aqueous poly(vinyl alcohol) solution (12% PVA with a degree of hydrolysis>80%) was obtained from Holland Novochem in the Netherlands. The carbohydrate was mixed into the aqueous poly(vinyl alcohol) solution and the resulting aqueous solution of carbohydrate and poly(vinyl alcohol) was added to the urea melt, where after the melt was particulated. The added carbohydrates were fructose and HFS42, which is a commonly available syrup comprising 71 wt % dry matter and 29 wt % water, where the dry matter comprises 42 wt % fructose, 53 wt % dextrose, 2.5 wt % maltose, 1 wt % malotriose, and 1.5 wt % polysaccharides. The combinations of carbohydrate and poly(vinyl alcohol) were compared with urea without additive and the standard product with urea-formaldehyde conditioning agent, UF80.

Table 2 shows the crushing strength, dust formation and caking index for urea, without additive, with urea-formaldehyde conditioning agent and with different combinations of carbohydrate and poly(vinyl alcohol).

TABLE 2

| Additive | Crushing Strength (kgf) | Dust formation (mg/kg) | Caking Index |
| --- | --- | --- | --- |
| no additive | 1.5 | 800 | 205 |
| 1 wt % UF80 | 3.6 | 400 | 30 |
| 0.1 wt % PVA solution + 0.2 wt % fructose | 3.5 | 25 | 0 |
| 0.1 wt % PVA solution + 0.2 wt % HFS42 | 2.5 | 225 | 166 |
| 0.1 wt % PVA solution + 0.4 wt % HFS42 | 3.8 | 125 | 44 |

This experiment demonstrates that the addition of a combination of poly(vinyl alcohol) and carbohydrate to a urea melt results in urea particles with improved crushing strength, low caking tendency and low dust formation.

Experiment 3

An aqueous poly(vinyl alcohol) solution (12% PVA with a degree of hydrolysis>80%) was obtained from Holland Novochem in the Netherlands. The carbohydrate was mixed into the aqueous poly(vinyl alcohol) solution and the resulting aqueous solution of carbohydrate and poly(vinyl alcohol) was added to the urea melt, where after the melt was particulated. The added carbohydrates were fructose and HFS42. The combinations of carbohydrate and poly(vinyl alcohol) were compared with urea without additive and with the standard product with urea-formaldehyde, UF80. In this experiment, the concentration of the urea melt was more than 99 w/w % urea and less than 1 w/w % water.

Table 3 shows the crushing strength, dust formation and caking index for urea, without additive, with urea-formaldehyde conditioning agent and with different combinations of carbohydrates and poly(vinyl alcohol).

TABLE 3

| Additive | Crushing Strength (kgf) | Dust formation (mg/kg) | Caking Index |
|---|---|---|---|
| no additive | 1.5 | 800 | 205 |
| 1 wt % UF80 | 3.6 | 400 | 30 |
| 0.1 wt % PVA solution + 0.4 wt % HFS42 | 4.0 | 125 | 61 |
| 0.15 wt % PVA solution + 0.3 wt % HFS42 | 3.8 | 25 | 28 |
| 0.075 wt % PVA solution + 0.15 wt % HFS42 | 4.7 | 50 | 0 |
| 0.075 wt % PVA solution + 0.075 wt % fructose | 2.8 | 75 | 28 |

This experiment demonstrates that the addition of a combination of poly(vinyl alcohol) and carbonate to a urea melt results in urea particles with improved crushing strength, low dust formation and caking tendency, when an almost pure urea melt is used for particulation.

The present invention shows that it is possible to improve the crushing strength, reduce the dust formation and the caking tendency of urea particles by the addition of at least one carbohydrate, with or without a polyvinyl compound, to the urea melt before particulation. The urea melt obtained by the method according to the present invention can be particulated by all common particulation methods. For certain particulation methods, for instance in fluid bed granulation processes, it could be possible to have a higher granulation temperature compared to granulation of urea without additive or with commonly used additives.

The additives according to the present invention can easily be added to the urea melt and do not require a preformed particle. The carbohydrates might be added to the urea melt as solids, they might be dissolved in a solvent or an aqueous solution of the polyvinyl compound or a urea solution before being added to the urea melt. The required amounts of the additives according to the present invention are lower than most other conditioning agents, and the toxicity is much lower than for the commonly used conditioning agent, formaldehyde.

The invention claimed is:

1. A method of improving the crushing strength and reducing the dust formation and the caking tendency of urea particles which comprises adding
at least one carbohydrate and optionally a polyvinyl compound to molten urea.

2. A method according to claim 1,
wherein
the carbohydrate added is selected from the group consisting of monosaccharide, disaccharide, oligosaccharide, polysaccharide and a mixture thereof.

3. A method according to claim 1,
wherein
at most 5 wt % carbohydrate, based on the amount of urea, is added.

4. A method according to claim 1,
wherein
0.02-2 wt % carbohydrate, based on the amount of urea, is added.

5. A method according to claim 1,
wherein
a polyvinyl compound of the general formula $(CHX-CHY)_n$, where n=4-10 000, and X and Y independently of one another are selected from the group consisting of a hydrogen atom and a polar organic group, is added.

6. A method according to claim 5,
wherein the polar organic group is selected from the group consisting of a carboxylic acid group, an ester group, a hydroxyl group, an amine group and an amide group.

7. A method according to claim 6, wherein X is a hydrogen atom and at least 70% of Y consists of a hydroxyl group.

8. A method according to claim 1,
wherein
an aqueous solution of the polyvinyl compound having a concentration of from 0.01 to 1 wt %, based on the amount of urea, is added.

9. A method according to claim 8,
wherein
an aqueous solution of the polyvinyl compound having a concentration of from 0.05 to 0.5 wt %, based on the amount of urea, is added.

10. A method according to claim 1,
wherein
the carbohydrate is added to the urea as a solid, or is dissolved in a solvent or an aqueous solution of the polyvinyl compound or a urea solution before being added to the urea.

11. A method according to claim 7, wherein at least 80% of Y consists of a hydroxyl group.

* * * * *